US012629110B2

(12) United States Patent
González Martínez et al.

(10) Patent No.: US 12,629,110 B2
(45) Date of Patent: May 19, 2026

(54) DEVICE FOR THE DETECTION OF GAMMA RAYS BASED ON SEGMENTED METASCINTILLATOR BLOCK DETECTORS

(71) Applicants: MULTIWAVE METACRYSTAL S.A., Plan les Ouates-Geneva (CH); CONSEJO SUPERIOR DE INVESTIGACIONES CIENTÍFICAS (CSIC), Madrid (ES); UNIVERSITAT POLITÈCNICA DE VALÈNCIA, Valencia (ES)

(72) Inventors: Antonio Javier González Martínez, Valencia (ES); Paul Lecoq, Chevry (FR); José Maria Benlloch Baviera, Valencia (ES); Georgios Konstantinou, Plan les Ouates-Geneva (CH); John Barrio Toala, Valencia (ES)

(73) Assignees: MULTIWAVE METACRYSTAL S.A, Plan les Ouates-Geneva (CH); CONSEJO SUPERIOR DE INVESTIGACIONES CIENTÍFICAS (CSIC), Madrid (ES); UNIVERSITAT POLITÈCNICA DE VALÈNCIA, Valencia (ES)

( * ) Notice: Subject to any disclaimer, the term of this patent is extended or adjusted under 35 U.S.C. 154(b) by 246 days.

(21) Appl. No.: 18/699,518

(22) PCT Filed: Oct. 7, 2022

(86) PCT No.: PCT/EP2022/077956
§ 371 (c)(1),
(2) Date: Apr. 8, 2024

(87) PCT Pub. No.: WO2023/057630
PCT Pub. Date: Apr. 13, 2023

(65) Prior Publication Data
US 2024/0427031 A1     Dec. 26, 2024

(30) Foreign Application Priority Data

Oct. 7, 2021    (EP) ..................................... 21382902

(51) Int. Cl.
| | |
|---|---|
| *G01T 1/20* | (2006.01) |
| *A61B 6/03* | (2006.01) |
| *G01T 1/29* | (2006.01) |

(52) U.S. Cl.
CPC ............ *A61B 6/037* (2013.01); *G01T 1/2002* (2013.01); *G01T 1/2008* (2013.01); *G01T 1/20186* (2020.05); *G01T 1/2985* (2013.01)

(58) Field of Classification Search
None
See application file for complete search history.

(56) References Cited

U.S. PATENT DOCUMENTS

| | | | | |
|---|---|---|---|---|
| 4,677,299 A * | 6/1987 | Wong | .................... | G01T 1/2985 |
| | | | | 250/363.04 |
| 7,102,135 B2 * | 9/2006 | Lecoq | .................. | G01T 1/2985 |
| | | | | 250/361 R |

(Continued)

FOREIGN PATENT DOCUMENTS

| | | |
|---|---|---|
| EP | 4033271 A1 | 7/2022 |
| JP | 2000-206254 A | 7/2000 |

OTHER PUBLICATIONS

P. Lecoq, "Pushing the Limits in Time-of-Flight PET Imaging", Journal, 2017, 473-485, vol. 1, No. 6, IEEE Transactions on Radiation and Plasma Medical Sciences.

(Continued)

*Primary Examiner* — Thomas R Artman
(74) *Attorney, Agent, or Firm* — Hayes Soloway PC

(57) ABSTRACT

A device for the detection of gamma rays to be used primarily in a PET scanner is based on a scintillator hetero-structure combining the high stopping power of scintillators (Continued)

commonly used in PET scanners (such as L(Y)SO, BGO, etc.) and fast scintillators based on polymers loaded with fast emitting dyes or nanocrystals, or thin layers of nanocrystals or multiple quantum well structures. While the metascintillator block is read out in the monolithic or semi-monolithic arrangement, the fast scintillator is segmented so that it is read out by less photodetectors. The particular arrangement of this detector module allows combining all the important features of a high-performance Time-of-Flight PET (TOF-PET) detector module, i.e. a high photoelectric detection efficiency for the gamma rays, a precise 3D information (including the depth of interaction DOI) of the gamma ray conversion in the module, good energy resolution and superior timing resolution.

15 Claims, 3 Drawing Sheets

(56) References Cited

U.S. PATENT DOCUMENTS

| | | | | |
|---|---|---|---|---|
| 7,304,309 | B2 * | 12/2007 | Suhami | G02B 6/1225 |
| | | | | 250/370.11 |
| 7,671,339 | B2 * | 3/2010 | Shibuya | G01T 1/2985 |
| | | | | 250/363.04 |
| 8,115,173 | B2 * | 2/2012 | Eriksson | G01T 1/2008 |
| | | | | 250/367 |
| 8,183,533 | B2 * | 5/2012 | Nelson | G01T 1/2008 |
| | | | | 250/361 R |
| 8,299,437 | B2 * | 10/2012 | Nakamura | G01T 1/1642 |
| | | | | 250/361 R |
| 8,466,418 | B2 | 6/2013 | Nakamura | |
| 2004/0129886 | A1 * | 7/2004 | Lecoq | G01T 1/2008 |
| | | | | 250/363.03 |
| 2006/0202125 | A1 * | 9/2006 | Suhami | G01T 1/202 |
| | | | | 250/368 |
| 2009/0121141 | A1 * | 5/2009 | Eriksson | G01T 1/2985 |
| | | | | 250/361 R |
| 2009/0134334 | A1 * | 5/2009 | Nelson | G01T 1/202 |
| | | | | 250/361 R |
| 2009/0159804 | A1 * | 6/2009 | Shibuya | G01T 1/2985 |
| | | | | 250/363.04 |
| 2010/0301221 | A1 * | 12/2010 | Nakamura | G01T 1/1642 |
| | | | | 250/366 |
| 2011/0127435 | A1 * | 6/2011 | Nakamura | G01T 1/1644 |
| | | | | 250/363.04 |
| 2016/0216381 | A1 * | 7/2016 | Nishihara | G01T 1/2002 |
| 2023/0075571 | A1 * | 3/2023 | Lecoq | G01T 1/2008 |
| 2024/0427031 | A1 * | 12/2024 | González Martínez | |
| | | | | G01T 1/2985 |

OTHER PUBLICATIONS

Maurizio Conti, "Focus on time-of-flight PET: the benefits of improved time resolution", Journal, 2011, 1147-1157, vol. 38, European Journal of Nuclear Medicine and Molecular Imaging.

Maurizio Conti, "The new opportunities for high time resolution clinical TOF PET", Journal, 2019, 139-147, vol. 7, Clinical and Translational Imaging.

siemens-healthineers.com, "Biograph Vision PET/CT—Precision-driven Performance", Brochure, 2022, [online] <https://usa.healthcare.siemens.com/molecular-imaging/pet-ct/biograph-vision><retrieved on Apr. 2, 2024>.

Georgios Konstantinou, "Metascintillators for Ultrafast Gamma Detectors: A Review of Current State and Future Perspectives", Journal, 2022, 5-11, vol. 6, No. 1, IEEE Transactions on Radiation and Plasma Medical Sciences.

Georgios Konstantinou, "Subsurface Laser Engraving Techniques for Scintillator Crystals: Methods, Applications, and Advantages", Journals, 2017, vol. 1, No. 5, IEEE Transactions on Radiation and Plasma Medical Sciences.

R. M. Turtos, "Towards a metamaterial approach for fast timing in PET: experimental proof-of-concept", Journal, 2019, 1-12, vol. 64, Physics in Medicine and Biology.

Neus Cucarella, John Barrio, "Timing evaluation of a PET detector block based on semi-monolithic LYSO crystals", Article, 2021, 8010-8023, vol. 48, Medical Physics.

Matteo Salomoni, "Enhancing Light Extraction of Inorganic Scintillators Using Photonic Crystals", Journal, 2018, 1-35, vol. 8, No. 78, Crystals.

* cited by examiner

DEVICE FOR THE DETECTION OF GAMMA RAYS BASED ON SEGMENTED METASCINTILLATOR BLOCK DETECTORS

CROSS-REFERENCE TO RELATED APPLICATIONS AND PRIORITY

This patent application claims priority from PCT Application No. PCT/EP2022/077956 filed Oct. 7, 2022, which claims priority from European Patent Application No. 21382902.1 filed Oct. 7, 2021. Each of these patent applications are herein incorporated by reference in their entirety.

FIELD OF THE INVENTION

The invention relates to a device for the detection of gamma rays. The device of the invention can be applied, preferably but without limitation, to positron-emission tomography (PET) scanner technologies.

BACKGROUND OF THE INVENTION

Current techniques for in-vivo molecular imaging, such as time-resolved quantitative multiparametric imaging, pharmacodynamic studies or in-vivo tracking of a small number of cells for stem-cell tissue repair therapy, cancer immunotherapy, etc., can highly benefit from achieving improved molecular sensitivities and processing speeds. In this context, high-precision Time-of-Flight PET (TOF PET) scanners are very promising technologies able to provide a substantial increase in the signal-to-noise ratio of the reconstructed images, as well as allowing the possibility to achieve very high sensitivities in PET scanners at the sub-picomolar level (see P. Lecoq, "*Pushing the limits in Time-Of-Flight PET imaging*", IEEE T. Radiat. Plasma Med. Sci., Vol. 1, No. 6 (2017) 473-485).

When studying gamma-ray interactions, the localization of the emission point of an annihilation pair along a line-of-response (LOR), defined by the nearly coincident detection of a pair of annihilation gamma rays, depends on the detection time difference between the two annihilation photons (also known as the time-of-flight (TOF) difference of the photons), whose accuracy is given by the coincidence time resolution (CTR) of a detection chain. It is well known that this information allows reducing the noise 'variance associated to the "3D-PET ill-posed tomographic inversion problem" by a factor proportional to the CTR reduction:

$$\left(\frac{SNR_{TOF}}{SNR_{nonTOF}}\right)^2 = \frac{2D}{c \times CTR},$$

where D is the diameter of the field-of-view (FOV) and c is the speed of light in vacuum (see M. Conti, "*Focus on Time-of-Flight PET: the benefits of improved time resolution*", Eur J. of Nuc. Med. Mol. Imaging, (2011) 38, 1147-1157). This variance gain is associated to a similar gain (G) in the effective sensitivity of the PET scanner (see M. Conti, B. Bendriem "*The new opportunities for high time resolution clinical TOF PET*", Clinical and Translational Imaging (2019) 7:139-147), given by the formula:

$$G_{sens} = \left(\frac{SNR_{TOF}}{SNR_{nonTOF}}\right)^2 \Big/ 1.47.$$

A CTR resolution of 100 ps would improve the effective sensitivity of the PET scanner by a factor of about 2, as compared to the best TOFPET scanner today (currently, Biograph Vision™ from Siemens, see for example: https://usa.healthcare.siemens.com/molecular-imaging/pet-ct/biograph-vision), and by a factor of 18.1 for a 40 cm diameter FOV, as compared to a PET scanner with no TOF capability. Would the CTR reach 10 ps, the sensitivity gain would be 180, as compared to a non-TOFPET, and more than 20, as compared to Biograph Vision™, respectively.

Moreover, achieving a CTR of about 10 ps FWHM ("full width at half maximum") would allow to obtain a direct three-dimensional (3D) volume representation of the estimated activity distribution of a positron-emitting radiopharmaceutical, at the mm level and without the need for tomographic inversion. This would constitute a remarkable improvement in PET imaging and quantification.

A two-order of magnitude gain in the effective sensitivity would have the following consequences for PET scanners:
 reduction of the radiation doses of molecular imaging procedures to negligibly low levels;
 reduction of the synthesized quantity of radiopharmaceutical needed for each examination and, thus, of the relatively high cost currently associated with in-vivo molecular imaging procedures;
 further extension of the benefit of molecular-imaging procedures beyond oncology towards cardiovascular, neurological, metabolic, inflammatory, infectious, or metabolic disease (such as diabetes) medicine, including in the pediatric, neonatal, and prenatal medicine;
 maximizing the spatial and temporal resolution of PET-based molecular imaging;
 precise dynamic studies of molecular processes of high interest in pharmacology, for screening and selecting candidate molecules for the next generation of drugs or new applications thereof;
 potentially further extension of molecular in-vivo imaging to study "systems biology" of the whole human body, through whole-body high precision TOFPET imaging systems;
 avoidance of the need of full-angular coverage of the patient for imaging procedures, opening many new opportunities for PET system designs.

In order to improve the time resolution of TOFPET scanners, the concept of "metascintillators" has been recently proposed by the inventors of this patent application (see G. Konstantinou, P. Lecoq, J. M. Benlloch and A. J. Gonzalez, "Metascintillators for ultra-fast gamma detectors: a review of current state and future perspectives," in IEEE Transactions on Radiation and Plasma Medical Sciences, doi: 10.1109/TRPMS.2021.3069624).

A metascintillator is a structure composed of a combination of scintillating materials, a dense one chosen for its increased probability of capturing incoming gamma, and a fast one chosen for its quick production of optical photons that improves timing resolution of the system. The energy of a gamma captured in the dense scintillator leaks to the fast one through a travelling recoil electron, with its amount following the stochastic distribution of energy sharing. The statistical probability of this leakage is increased if the materials are found in close proximity, smaller than the mean range of the recoil electron, which is less than 500 µm.

This energy leaking, or sharing, has a stochastic nature. However, when the fast emitter is a material with prompt photon production capabilities, even a small percentage of energy sharing is sufficient to lead to the production of prompt photons which can greatly improve the timing resolution of the detector. Furthermore, the two materials can be substantially isolated on the optical level. In every case, the photons produced are propagated towards the photodetector, a device which transforms optical photons to a measurable electric signal. The scintillators are optically coupled to the photodetector, through the application of materials such as optical grease, optical cement or other similar compounds, which are transparent for the wavelength of the produced photons. Any such material, solid, viscous, gas or liquid can be used to provide optical coupling. Optical coupling media can be separated along with the shape of the scintillators or provide a uniform structure which leads to limited or controlled optical transport between the different scintillators, through light guides.

Existing photodetector technologies refer to preferably silicon photomultipliers but also arrays of single photon avalanche diodes, avalanche photodiodes, photomultiplier tubes, micro-channel plate photomultiplier tubes and any technology transforming optical energy to measurable electric signals.

Light produced in the scintillators is propagated towards the photodetectors. Commercial models generally have dimensions between 1 and 6 mm$^2$ and are commonly prepared in arrays, either unidimensional between 1 by 2 to 1 by 16 or bi-dimensional, 2 by 4 to 16 by 16. Other dimensions and array arrangements are possible for different technologies, but the principle is substantially similar.

Using reflectors or, more generally, optical barriers to limit the light spread is a proved way to further improve timing. Such optical barriers comprise diffuse reflecting materials such as Teflon, commercial enhanced specular detectors, materials with different refractive index to harness the total internal reflection of the high refractive index scintillating materials, sub-surface laser engraved patterns (Konstantinou, G., et al. "Subsurface laser engraving techniques for scintillator crystals: Methods, applications, and advantages." IEEE Transactions on Radiation and Plasma Medical Sciences 1.5 (2017): 377-384), photonic crystal slabs and different metamaterials, and Bragg reflectors.

In radiation detectors, the standard approach is a detector where scintillators have been cut in oblong parallelepiped shapes, of dimensions such as 2×2×20 mm$^3$, in what is called pixelated detectors. Scintillating pixels are optically isolated from each other in a configuration that generally leads to good timing of the order of 200 ps coincidence time resolution using LYSO crystals, but without an obvious way of detecting the position of interaction of the gamma photon within the pixel. Furthermore, the inclusion of reflectors increases the non-scintillating material of the detector, reducing its efficiency. As an answer to that, monolithic scintillators have recently been proposed. In this configuration, a bigger scintillator of dimensions such as 50×50×20 mm$^3$ is optically coupled to several photodetectors. The distribution of photons on the photodetectors leads to an accurate reconstruction of the scintillation event onset localization, however the timing of the detector is relatively compromised by the big optical space available which leads to an abundance of available optical paths and spread of light over several SiPMs, increasing in such a way the time spread of photon detection between different events. Coincidence timing resolution is normally of the order of 400-500 ps for LYSO monolithic crystals, however the advantages of monolithic and semi-monolithic (when the block approach is followed in only one dimension) approaches is the sub-millimeter localization of the x-y-z location of the scintillation onset. In both monolithic and semi-monolithic cases, the blocks are optically separated from each other, meaning that light is either substantially confined within each block, or is controllably allowed to be shared between blocks through the use of semi-transparent/translucent separators or light guides between the block and the photodetectors.

Other gamma-ray detection setups are disclosed, for instance, in the article by Turtos, R. M., et al., "Towards a metamaterial approach for fast timing in PET: experimental proof-of-concept", Phys. In Med. & Bio., vol. 64, No. 18 (19.09,2019), p. 185018, or in patent publications U.S. Pat. No. 8,466,418 B2 and JP 2000-206254 A, where several combinations of stacked materials suitable for tomography techniques are described. However, in order to clearly define the location of the initial gamma interaction, these documents require more than one photodetector optically connected to a scintillator. Unfortunately, in that case the possible optical paths for the produced photons increase, as well as the noise associated to the photodetectors used for the gamma interaction localization, yielding to a degradation of the timing resolution. On the other hand, in these detectors, scintillators are divided by separators to create a 1-to-1 match with respective photodetectors, limiting the availability of gamma interaction location information.

SUMMARY OF THE INVENTION

In the light of the problems of the state of the art set forth in the previous section, the present invention proposes a device for the detection of gamma rays according to any of the embodiments disclosed in the claims. Said device comprises, preferably, at least one metascintillator block detector, wherein said metascintillator block detector comprises:

- a stack of alternate dense scintillator layers and fast scintillating material layers; wherein the fast scintillator layers are segmented in optically separated sectors; and
- a plurality of arrays of photodetectors optically coupled to the stack.

Advantageously in the invention, each dense scintillator layer is coupled to at least two photodetectors; and each sector of the fast scintillator layer is coupled to less photodetectors than the adjacent dense scintillator layers in the stack. As a result, the fast scintillation light is directed through the partially isolated optical space of the fast scintillator, to a small number of photodetectors, thus limiting the optical space and corresponding optical paths and, in this way, increasing the quality of timing information, leading to improved timing resolution for the detection device.

In the context of the invention, a dense scintillator layer is any layer material, or combination of materials, having a density substantially equal or above 5 g/cm$^3$ (more preferably, between 5 and 10 g/cm$^3$) and an effective atomic number substantially equal or above 50.

In the context of the invention, a fast scintillator layer is any layer material, or combination of materials, having a scintillation production rate of at least 80 photons per 100 keV of energy deposited in less than 1 ns.

In the context of the invention, the expressions "optically coupled" and "optically separated", when referred to any two elements, will be understood as those elements allowing optical photon transmission there between or not, respectively.

In a preferred embodiment of the invention, the dense scintillator layers comprise BGO, LSO, LYSO, GSO, NaI, CsI, BaF2, LuAP, LuAG and/or GGAG scintillation materials, alone or in combination.

In a further preferred embodiment of the invention, the fast-scintillating material layers comprise BaF2, CdSe, PVT-PPP, MAPbBr3, ZnO or any kind of ultrafast (<5 ns) scintillation materials, alone or in combination.

In a further preferred embodiment of the invention, the dense scintillator layers and fast scintillating material layers have at least one dimension smaller than 500 μm.

In a further preferred embodiment of the invention, the plurality of arrays of photodetectors optically coupled to the stack comprises a single bi-dimensional array.

In a further preferred embodiment of the invention, the plurality of arrays of photodetectors comprises a pair of bi-dimensional arrays which are optically coupled to opposite sides of the stack.

In a further preferred embodiment of the invention, the plurality of arrays of photodetectors comprises two single-dimensional arrays which are optically coupled to two sides of the stack with smallest dimensions.

In a further preferred embodiment of the invention, each sector of the fast scintillator layers is coupled to a single photodetector per side.

In a further preferred embodiment of the invention, each sector of the fast scintillator layers is coupled to two photodetectors per side.

In a further preferred embodiment of the invention, the sectors of the fast scintillator layers are isolated one from another with the mechanical separation of the segments, without the application of reflective materials.

In a further preferred embodiment of the invention, the sectors of the fast scintillator layers of the metascintillator block detector are optically isolated from each other or from the adjacent dense scintillation layers with the use of reflecting materials on at least one of the surfaces.

In a further preferred embodiment of the invention, the reflecting materials comprise Bragg reflectors.

In a further preferred embodiment of the invention, the reflecting materials comprise Photonic Crystal slabs.

In a further preferred embodiment of the invention, the reflecting materials allow partial sharing of light in a controlled manner.

DESCRIPTION OF THE DRAWINGS

The foregoing and other features and advantages will be more fully understood from the detailed description of the invention, as well as from the preferred embodiments referring to the attached figures, which are described in the following paragraphs, wherein.

Figures 1, 2:
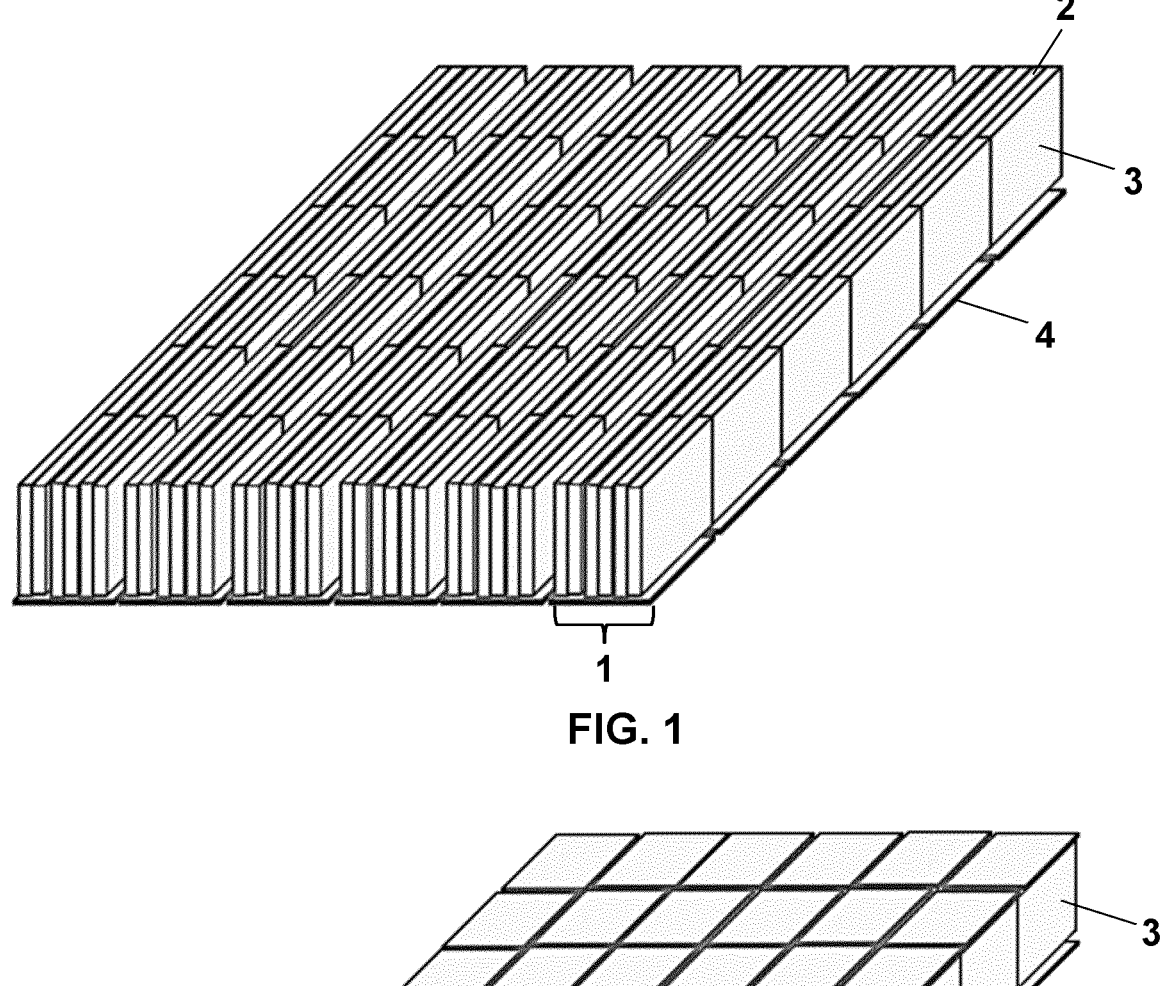
FIG. 1 depicts a preferred embodiment of a segmented metascintillator block detector, configured as a stack of alternate layers of dense and fast scintillators, wherein the photodetectors array optically coupled to the stack comprises a single bi-dimensional array and the fast scintillators are segmented to a 1-to-1 matching with the photodetector.
FIG. 2 depicts a preferred embodiment of a segmented metascintillator block detector, wherein the plurality of arrays of photodetectors comprises a pair of bi-dimensional arrays which are optically coupled to opposite sides of the stack.

NUMERICAL REFERENCES USED IN THE DRAWINGS (1) Gamma-ray metascintillator block detector
(2) Dense scintillator layers
(3) Fast scintillating material layers
(4) Photodetectors
(5) Optical reflector element

DETAILED DESCRIPTION OF THE INVENTION

As described in the background section, an existing problem in radiation detectors is that, in order to clearly define the location of the initial gamma interaction, more than one photodetector should be optically connected to a scintillator. Unfortunately, in that case the possible optical paths for the produced photons increase, as well as the noise associated to the photodetectors used for the gamma inter-action localization, yielding to a degradation of the timing resolution. On the other hand, the common approach of pixilation, where scintillators are divided by separators to create a 1-to-1 match with respective photodetectors, limits the availability of gamma interaction location information. The solutions for precise depth-of-interaction (DOI) determination are either expensive (double readout) or incompatible with good timing (light sharing).

The proposed block detector/pixel technology creates a hybrid readout approach where a metascintillator architecture allows the light produced by slow and dense scintillator components to be shared, providing depth-of-interaction information with good resolution, while the majority of fast light that carries the timing information is directed to a smaller number or even a single photodetector, also providing a more accurate timing characterization. The way to achieve this is through a metascintillator block detector (1), wherein said metascintillator block detector (1) comprises a stack of alternate dense scintillator layers (2) and fast scintillating material layers (3), and a plurality of arrays of photodetectors (4) optically coupled to the stack of dense scintillator (2) and fast scintillating material (3) layers. Each dense scintillator layer (2) is optically coupled to a plurality of photodetectors. This way, the initial gamma interaction location can be deduced accurately through the distribution of light in the photodetector array. The device is character-ized in that the fast scintillating (3) layer is segmented in sectors, where these sectors are preferably understood as longitudinal portions of the fast-scintillating material layers (3) defined over the plane thereof, as shown in FIGS. 1-5. These sectors are optically separated from each other and optically coupled to less photodetectors than the closest dense scintillator layers. This means that the fast scintillation light is directed through the partially isolated optical space of the fast scintillator, to a small number of photodetectors, limiting the optical space and corresponding optical paths, and in this way increasing the quality of timing information, leading to improved timing resolution for the detection system. Metascintillators have already shown the potential of improving the coincidence timing resolution of pixelated detectors down to close to 100 ps. With the combination of semi-monolithic segmented metascintillators, the timing is the same as in pixelated detectors, while the advantages of monolithic and semi-monolithic approaches on sub-millimeter localization of the x-y-z of the scintillation event onset, are also retained.

The dense scintillator layers (2) preferably comprise BGO, LSO, LYSO, GSO, NaI, CsI, BaF2, LuAP, LuAG and/or GGAG scintillation materials, alone or in combination. These materials are chosen for their capability to stop the majority of incoming gammas. Their respective light yield is of secondary importance, as their role is to stop the gamma and, in this way increase the detection efficiency of the system. Another advantage of the structure is that even when some gamma photons interact through Compton scattering, the ensuing gamma photons are less energetic, which means that the probability of them being captured directly by the fast scintillator is increased.

The fast-scintillating material layers (3) preferably comprise BaF2, CdSe, PVT-PPP, MAPbBr3, ZnO, CdSe/PVT or any kind of ultrafast (<5 ns decay time) scintillation materials, alone or in combination, in the form of bulk scintillators, thin layers or nanocrystals. These materials might have reduced detection efficiency due to their low effective atomic number. However, as described above, the power of the metascintillator topology is that they will still participate in the photon production. Particular materials, such as the plastic scintillators (PVT-PPP) or nanoplatelets and quantum dots (CdSe) comprise a combination of materials themselves; the scintillating molecules are embedded in transparent and atomically coupled hosts in order to avoid increased photon absorption.

The dense scintillator layers (2) and fast scintillating material layers (3) have at least one dimension smaller than 500 μm. This is necessary for the synergy between dense and fast scintillators, the foundation of the metascintillator paradigm. When a gamma photon is stopped in the dense material, an electron is kicked out of its stack and leaves the atomic structure as a recoil electron. This recoil electron loses energy while travelling in the scintillator, producing excitons which lead to the production of optical, detectable photons. The range of this electron is variable depending on the material, but measures within a few hundreds of micrometers. By bringing materials with one dimension within this order of magnitude, the stochastic probability of the recoil electron traversing both, hence producing photons in both, according to their kinetics, is improved.

In a preferred embodiment, the plurality of arrays of photodetectors (4) optically coupled to the stack comprises a single bi-dimensional array, as shown in FIG. 1. This embodiment carries the improved characteristic of allowing both excellent timing as well as scintillation event location detection. The first happens through using the fast photons of the fast scintillators, which are confined in the optical space of a single segment. The confinement reduces the optical paths available for the photons, reducing also the time spread between event onset and first photon detection between different events. The second is an added advantage, which results from the photons of the dense scintillator being distributed among the several coupled photomultipliers. As demonstrated in prior art ((J. Barrio, et al., Medical Physics 2021), the distribution allows precise x-y-z localization of the photon production area. Particularly for the case of DOI, this is a significant improvement on existing approaches, which can further improve the timing of the system, as knowledge on the initial location of gamma interaction can provide correction values for the measured optical photon detection.

In another preferred embodiment, the plurality of arrays of photodetectors (4) comprises a pair of bi-dimensional arrays which are optically coupled to opposite sides of the stack, as depicted in FIG. 2. The advantage of this approach is that every scintillation event is read-out by more photodetectors (4), improving the resolution of the event localization. On top of that, by analyzing the Cramer-Rao timing limit for scintillators, we see that having more than one photodetector (4) connected to the small optical space of the fast scintillator segment can further improve the timing resolution of the system, along with providing a second estimator for DOI.

Figure 3:
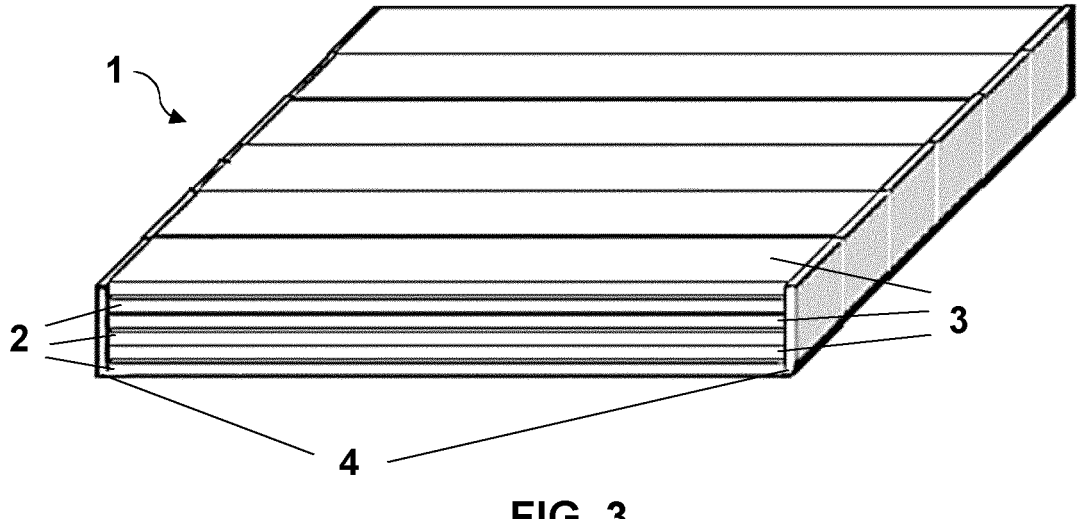
FIG. 3 depicts a preferred embodiment of a segmented metascintillator block detector, wherein the plurality of arrays of photodetectors comprises two single-dimensional arrays which are optically coupled to two sides of the stack with smallest dimensions.

In another preferred embodiment, the plurality of arrays of photodetectors (4) comprises two single-dimensional arrays which are optically coupled to two sides of the stack with smallest dimensions, as depicted in FIG. 3. This approach combines the characteristics of the previous embodiment, adding on top of that the capability to stack the metascintillators in a direction perpendicular to the direction of the incoming gamma photon, which can affect positively the stochastic characteristics of energy sharing. Moreover, to improve the gamma detection efficiency and stopping power of the detector, we can stack a plurality of such devices along the direction of gamma photons, parallel to the sampling direction of the metascintillator.

Figure 4:
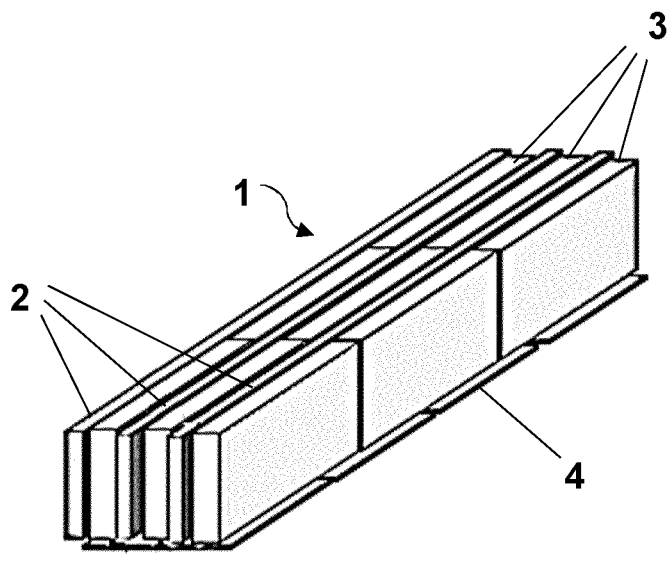
FIG. 4 depicts a detail of a preferred embodiment of a segmented metascintillator block detector wherein each fast scintillator segment is coupled to two photodetectors per side.

In a preferred embodiment, each sector of the fast scintillator layers is coupled to a single photodetector per side, for the reasons described in the previous three paragraphs. However, in another preferred embodiment, each sector of the fast scintillator layers is coupled to two photodetectors per side, as shown in the detail of FIG. 4. This approach allows more than one photodetectors to read-out the fast scintillator photons, providing a more robust statistical measure for the time of scintillation event onset. Such coupling can correspond to the 3:4 ratio between segments and photodetectors depicted in FIG. 4. However, different ratios can be considered, such as 2:3, 1:2 or other ratios.

In a preferred embodiment, the sectors of the fast scintillating material layers (3) are isolated one from another with the mechanical separation of the segments, without the application of reflective materials. This allows the high refractive index of the scintillating component, usually between 1.5 and 2.5, to guide the light within the segment through the mechanism of total internal reflection (TIR). From classical optics, Snell's law, the angle of extraction over a surface for the photons is a function of the refractive indices of the materials on the two sides of the surface. Given that with mechanical segmentation, the segments are substantially surrounded by air (refractive index 1), this angle is high enough to keep the light inside their confined optical space, with the aforementioned desired characteristics. This stands for the space between the segments, as well as between the fast and dense scintillating pieces.

Figure 5:
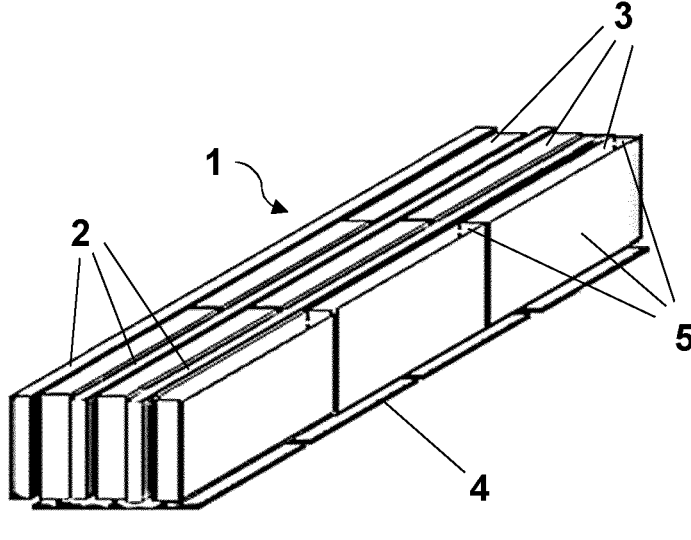
FIG. 5 depicts a detail of a preferred embodiment of a segmented metascintillator block detector wherein fast scintillator segments are covered with reflecting materials.

In a preferred embodiment, the sectors of the fast scintillating material layers (3) of the metascintillator block detector (1) are optically isolated from each other or from the adjacent dense scintillation layers (2) with the use of reflecting materials on at least one of the surfaces (5), as defined in FIG. 5. While TIR is a good solution for various configurations, while also being cost-effective, layering the segment surfaces with some reflecting material can be beneficial in more than one way, depending on the type of layering.

In a preferred embodiment, the reflecting materials (5) comprise Bragg reflectors. A distributed Bragg reflector (DBR) is a reflective structure formed from multiple layers of alternating materials with varying refractive indices, or some other characteristic (such as height) of a dielectric waveguide, resulting in periodic variation in the effective refractive index in the guide. The design of the Bragg reflector alters the behavior of the surface for light depending on the polarization and direction of the light. It can be transmissive, absorptive, reflecting or a probabilistic combination of the aforementioned.

In a preferred embodiment, the reflecting materials (5) comprise Photonic Crystal slabs. Photonic crystal slabs are slab-shaped periodic nanostructures that affect the effective distribution of the light in their proximity. They can interact with the light in different modes, essentially bending its direction in non-classical directions, or through resonance with particular wavelengths create conditions not found in nature, such as for instance a negative refractive index. Their application in scintillators is nascent and another patent application has been filed from some of the inventors of this application (EP21153601.6, Device for the detection of gamma radiation).

In a preferred embodiment, the reflecting materials (5) allow partial sharing of light in a controlled manner. This means that only a section of the respective surface is covered, either with one of the aforementioned reflectors, or the segments themselves are not mechanically separated but only optically, for instance with the application of subsurface laser engraved translucent barriers.

All of the above characteristics create a unique space of parameters and information channels, for the precise detection and characterization of both the x-y-z location and the time of a scintillation event onset. The device can be used for the detection and characterization of gamma rays, in particular for such in coincidence after an electron-positron annihilation event. Several devices of the described ones can be placed surrounding a subject under study which has been administered with a radiotracer including a positron emitter and a biological molecule. With the precision that the detector provides in the spatial and temporal domains, it is possible to reconstruct the distribution of the origin of the gamma pairs, through the reconstruction of their travel path (spatiality) and through the reconstruction of their temporal discrepancy (time-of-flight).

Such detection takes place through the combination of the time-series distributions of optical photons collected at the photodetector arrays (4). Such combination is performed either through theoretical, simulation or heuristic analysis of the time series, or either through the training of a neural network on similar theoretical, simulation or experimental datasets.

The invention claimed is:

1. A device for the detection of gamma rays comprising at least one metascintillator block detector, wherein said metascintillator block detector comprises:
   a layer stack of alternate dense scintillator layers and fast scintillating material layers; and a plurality of arrays of photodetectors optically coupled to the layer stack;

wherein each fast scintillating material layer is segmented in a plurality of sectors, said sectors being optically separated from each other, and also optically separated from the dense scintillator layers in the layer stack.

2. The device according to claim 1, wherein the dense scintillator layers comprise BGO, LSO, LYSO, GSO, NaI, CsI, BaF2, LuAP, LuAG and/or GGAG scintillation materials, alone or in combination.

3. The device according to claim 1, wherein the fast scintillating material layers comprise BaF2, CdSe, PVT-PPP, MAPbBr3, ZnO or any kind of ultrafast (<5 ns) scintillation materials, alone or in combination.

4. The device according to claim 1, wherein the dense scintillator layers and fast scintillating material layers have at least one dimension smaller than 500 μm.

5. The device according to claim 1, wherein the plurality of arrays of photodetectors optically coupled to the stack comprises a single bi-dimensional array.

6. The device according to claim 1, wherein the plurality of arrays of photodetectors comprises a pair of bi-dimensional arrays which are optically coupled to opposite sides of the stack.

7. The device according to claim 1, wherein the plurality of arrays of photodetectors comprises two single-dimensional arrays which are optically coupled to two sides of the stack with smallest dimensions.

8. The device according to claim 1, wherein each sector of the fast scintillating material layers is coupled to a single photodetector per side.

9. The device according to claim 1, wherein each sector of the fast scintillating material layers is coupled to two photodetectors per side.

10. The device according to claim 1, wherein the sectors of the fast scintillating material layers are isolated one from another with the mechanical separation of the segments, without the application of reflective materials.

11. The device according to claim 1, wherein the sectors of the fast scintillating material layers of the metascintillator block detector are optically isolated from each other or from the adjacent dense scintillation layers with the use of reflecting materials on at least one of the surfaces.

12. The device according to claim 11, wherein the reflecting materials comprise Bragg reflectors.

13. The device according to claim 11, wherein the reflecting materials comprise Photonic Crystal slabs.

14. The device according to claim 11, wherein the reflecting materials allow partial sharing of light in a controlled manner.

15. A method of use of the device according to claim 1 for the detection of gamma rays.

* * * * *